United States Patent [19]

Andersson

[11] Patent Number: 4,695,659
[45] Date of Patent: Sep. 22, 1987

[54] METHOD FOR DEALKYLATION OF ALKYL-ARYL ETHERS

[75] Inventor: Sven-Göran B. Andersson, Malmö, Sweden

[73] Assignee: Chemical Dynamics Development AB, Skara, Sweden

[21] Appl. No.: 881,027

[22] PCT Filed: Oct. 17, 1985

[86] PCT No.: PCT/SE85/00399

§ 371 Date: Jun. 20, 1986

§ 102(e) Date: Jun. 20, 1986

[87] PCT Pub. No.: WO86/02634

PCT Pub. Date: May 9, 1986

[30] Foreign Application Priority Data

Oct. 22, 1984 [SE] Sweden .................................. 8405262

[51] Int. Cl.⁴ ...................... C07C 37/00; C07C 37/055
[52] U.S. Cl. ...................................... 568/805; 568/806
[58] Field of Search ................................. 568/805, 806

[56] References Cited

U.S. PATENT DOCUMENTS 4,087,410  5/1978  Dominianni et al. ............... 568/766
4,112,003  9/1978  Huber .................................. 568/805
4,172,960  10/1979  Baldwin et al. ..................... 568/772

FOREIGN PATENT DOCUMENTS 1768050  3/1986  Fed. Rep. of Germany ...... 568/805
107714  12/1965  Norway ............................... 568/805
1227144  4/1971  United Kingdom .
2013653  8/1979  United Kingdom ............... 568/805

OTHER PUBLICATIONS

Bhatt et al., Tetrahedron Letters, vol. 25, No. 32, pp. 3497–3500 (1984).
Mincione, "Chemical Abstracts", vol. 73 (1970), p. 24547s.
Cabdidu et al., "Chemical Abstracts", vol. 78 (1973), p. 71603y.
Orgen et al., "Chemical Abstracts", vol. 83 (1975), p. 36919j.

Primary Examiner—Werren B. Lone
Attorney, Agent, or Firm—Dennison, Meserole, Pollack & Scheiner

[57] ABSTRACT

A method is disclosed for the dealkylation of alkylaryl ethers by reaction with aluminum triiodide under reflux. The reaction is carried out in the presence of a catalytic amount of a quaternary ammonium iodide in a substantially non-aqueous organic solvent. The reaction product is then hydrolyzed with water. The quaternary ammonium iodide can be of the formula $R_4N^+I^-$, wherein R is alkyl, and the solvent is preferably benzene or cyclohexane.

9 Claims, No Drawings

METHOD FOR DEALKYLATION OF ALKYL-ARYL ETHERS

The present invention relates to a method for dealkylation of alkyl-aryl ethers with aluminium iodide.

Dealkylation of ethers is a well known method in organic syntheses and many reagents can be used. Earlier methods have however considerable disadvantages when used on a technical scale. Hydrogen iodide, hydrogen bromide and hydrogen chloride as well as aluminium trichloride and ferrichloride give bad yields. Aluminium tribromide gives better yield but is an expensive raw material. Good yields can be obtained with boron trichloride, boron tribromide and boron triiodide but these reagents are very expensive and the methods are only of interest for laboratory work. Some phosphorus compounds can be used but are not very selective.

The use of aluminium triodide for dealkylation has earlier been tested. Aluminium metal and iodide reacted in carbon disulphide and the ether was then added in a carbon disulphide solution.

The disadvantages with this method is the use of the toxic and inflammable carbon disulphide and the rather long reaction times. Biproducts are formed, which in some cases have very bad smell and involve industrial hygiene problems.

The present method has important advantages as to industrial hygiene compared to the earlier known method and also gives a more pure product and higher yields. The reaction times are also shorter. The method is characterized by the use of inert solvents which are inexpensive and relatively easy to handle and the reaction takes place in the presence of catalytic amounts of a quaternary ammonium salt of the type $R_4N^+I^-$.

The reaction can be expressed as follows:

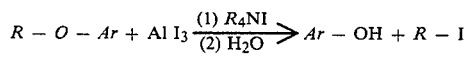

$R$ = alkyl
$Ar$ = aryl

The method will be further illustrated with the following examples:

EXAMPLE 1

Aluminium powder (2.5 g, 93 mmol) and iodine (19.0 g, 150 mmol) were mixed in 130 ml benzene (or cyclohexane) and were refluxed until the red colour of iodine disappeared (about 1.5 hours). The mixture was cooled. A solution of anisol (phenyl-methyl ether, 5.4 g, 50 mmol) and n-Bu$_4$N$^+$I$^-$ (tetra-n-butyl ammoniumiodide, 0.05 g, 0.14 mmol) dissolved in 25 ml benzene (cyclohexane) was added dropwise. The mixture was heated and was refluxed for 20 min, then cooled and hydrolysed with 150 ml water. The organic phase was separated and the water phase was extracted with 2×25 ml diethyl ether. The organic phases were collected and were extracted with 30 ml 2 molar NaOH. The water phase was separated, acidified with concentrated HCl and was extracted with 3×25 ml diethyl ether. The organic phases were dried (Na$_2$SO$_4$) and were evaporated to give pure crystalline phenol. Yield=99%. M.p. 41°–42° C.

EXAMPLE 2

Aluminium powder (75 g, 279 mmol) and iodine (57 g, 450 mmol) were mixed and refluxed as in example 1. After cooling a solution of pyrogalloltrimetylether, 1,2,3-trimetoxibenzene(8.4 g, 50 mmol) and n-Bu$_4$N$^+$I$^-$ (0.1 g, 0.28 mmol) in 25 ml benzene was added. After refluxing for 0.5 hours the mixture was hydrolyzed with 150 ml water. The benzene phase was separated and washed with 2×20 ml water, which was added to the water phase. The combined water phases were extracted with 6×50 ml ethylacetate(EtOAc). The EtOAc-phases were combined, dried (Na$_2$SO$_4$) and evaporated to give pure pyrogallol in a 95% yield. M.p. 132°–133° C.

The following table gives a survey of other dealkylations made according to the method.

| Ether | Solvents | Molar ratios AlI$_3$/ether | Molar ratios ether/R$_4$NI$^-$ | Reaction time (h) | Yield % | Product |
|---|---|---|---|---|---|---|
| anisol (C$_6$H$_5$OCH$_3$) | benzene | 1 | 360 | ⅓ | 100 | phenol (C$_6$H$_5$OH) |
| anisol (C$_6$H$_5$OCH$_3$) | cyclohexane | 1 | 360 | ⅓ | 100 | phenol (C$_6$H$_5$OH) |
| anisol (C$_6$H$_5$OCH$_3$) | CS$_2$ | 1 | 360 | ⅓ | 91 | phenol (C$_6$H$_5$OH) |

-continued

| Ether | Solvents | Molar ratios AlI$_3$/ether | Molar ratios ether/R$_4$NI$^-$ | Reaction time (h) | Yield % | Product |
|---|---|---|---|---|---|---|
| 2-methoxynaphthalene (naphthalene-OCH$_3$) | benzene | 1 | 360 | 1/3 | 94 | 2-hydroxynaphthalene (naphthalene-OH) |
| p-Methoxybenzaldehyde (CHO, OCH$_3$) | benzene | 1 | 360 | 1/2 | 78 | p-Hydroxybenzaldehyde (CHO, OH) |
| (CHO, OCH$_3$) | cyclohexane | 1 | 360 | 1/2 | 80 | p-Hydroxybenzaldehyde (CHO, OH) |
| m-methoxybenzaldehyde (CHO, OCH$_3$) | benzene | 1 | 360 | 1/2 | 84 | m-Hydroxybenzaldehyde (CHO, OH) |
| pyrogalloltrimethylether (OCH$_3$, OCH$_3$, OCH$_3$) | benzene | 3 | 180 | 1/2 | 95 | pyrogallol (HO, OH, OH) |
| vanilline (CHO, OCH$_3$, HO) | benzene | 4.8 | 360 | 1.5 | 88 | 2,3-Dihydroxybenzaldehyde (CHO, OH, OH) |
| Diphenylether | benzene | 1 | 360 | 1 | trace | phenol |
| ethoxybenzene (OC$_2$H$_5$) | cyclohexane | 1 | 360 | 1.0 | 90 | phenol (OH) |
| 4-Hydroxy-3-methoxytoluene (CH$_3$, OCH$_3$, OH) | cyclohexane | 2 | 100 | 0.7 | 98 | 3,4-Dihydroxytoluene (CH$_3$, OH, OH) |

| Ether | Solvents | Molar ratios AlI$_3$/ether | Molar ratios ether/R$_4$NI$^-$ | Reaction time (h) | Yield % | Product |
|---|---|---|---|---|---|---|
| isovanilline (CHO, OCH$_3$, OH) | cyclohexane | 5.5 | 120 | 2.5 | 14 | 3,4-Dihydroxybenzaldehyde (protocatechualdehyde) |
| 3,4-methylenedioxybenzaldehyde (piperonal) (heliotropin) | cyclohexane | 4.5 | 120 | 1.5 | 84 | 3,4-Dihydroxybenzaldehyde |
| 2,4,5-trimethoxybenzaldehyde | cyclohexane<br>″<br>″<br>″ | 1.5<br>3.3<br>5.5<br>10.0 | 100<br>100<br>100<br>50 | 14<br>1.5<br>1.5<br>10.0 | 88<br>90<br>91<br>85 | 4,5-Dimethoxysalicyl-aldehyde |
| 3,4,5-trimethoxybenzaldehyde | cyclohexane<br>″<br>″ | 1.5<br>3.3<br>5.5 | 12.0<br>6.0<br>15.0 | 7(1)<br>16(1)<br>10(1) | 1/ 41(2)<br>84(2)<br>81(2) | 4,5-Dimethoxy-2-hydroxybenzaldehyde<br>+<br>3,5-Dimethoxy-4-hydroxybenzaldehyde<br>2/ 3,4-Dihydroxy-5-methoxybenzaldehyde<br>+ |

Molar ratio ether/R$_4$NI$^-$ was 100 in all these experiments with 3,4,5-trimethoxylbenzaldehyde

| Ether | Solvents | Molar ratios AlI$_3$/ether | ether/R$_4$NI$^-$ | Reaction time (h) | Yield % | Product |
|---|---|---|---|---|---|---|
| | | | | | | 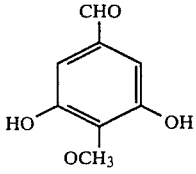 3,5-Dihydroxy-4-methoxybenzaldehyde |

What is claimed is:

1. In a process for the dealkylation of an alkyl aryl ether by reaction with aluminum triodide under reflux, the improvement comprising conducting said reaction in the presence of a catalytic amount of a quaternary ammonium iodide in a substantially non-aqueous organic solvent, and hydrolyzing the reaction product with water, whereby reaction time is shortened and reaction yield is increased.

2. Method according to claim 1, characterized in, that the quaternary ammonium salt has the general formula R$_4$N$^+$I$^-$, where R is an alkyl group.

3. Method according to claim 2, characterized in, that the quaternary ammonium salt is tetra-n-butylammonium iodide.

4. Method according to claim 1, 2 or 3, characterized in, that the reaction is conducted in an inert aliphatic, cycloaliphatic or aromatic solvent.

5. Method according to claim 4, characterized in, that the solvent is cyclohexane.

6. Method according to claim 4, characterized in, that the solvent is benzene.

7. Method according to claim 4, characterized in, that the solvent is toluene.

8. Method according to claim 4, characterized in, that the solvent is xylene.

9. Method according to claim 1, wherein the aluminum triodide is prepared in situ from iodine and aluminum powder.

* * * * *